(12) United States Patent
Cheng

(10) Patent No.: US 7,812,387 B2
(45) Date of Patent: Oct. 12, 2010

(54) TRENCH CAPACITOR

(75) Inventor: Kangguo Cheng, Beacon, NY (US)

(73) Assignee: International Business Machines Corporation, Armonk, NY (US)

( * ) Notice: Subject to any disclaimer, the term of this patent is extended or adjusted under 35 U.S.C. 154(b) by 37 days.

(21) Appl. No.: 12/062,310

(22) Filed: Apr. 3, 2008

(65) Prior Publication Data

US 2008/0185626 A1   Aug. 7, 2008

Related U.S. Application Data

(62) Division of application No. 11/380,693, filed on Apr. 28, 2006, now Pat. No. 7,410,862.

(51) Int. Cl.
H01L 27/108 (2006.01)
H01L 29/76 (2006.01)
H01L 29/94 (2006.01)
H01L 31/119 (2006.01)

(52) U.S. Cl. .................. 257/301; 257/300; 257/303; 257/296

(58) Field of Classification Search .................. 257/301, 257/300, 304, 349, 263, 266, 265, 287, 302, 257/303, 296
See application file for complete search history.

(56) References Cited

U.S. PATENT DOCUMENTS

| | | | |
|---|---|---|---|
| 5,849,638 A | 12/1998 | Ho et al. | |
| 5,891,807 A | 4/1999 | Muller et al. | |
| 6,140,175 A * | 10/2000 | Kleinhenz et al. | 438/243 |
| 6,190,988 B1 | 2/2001 | Furukawa et al. | |
| 6,232,171 B1 | 5/2001 | Mei | |
| 6,281,069 B1 * | 8/2001 | Wu et al. | 438/248 |
| 6,403,412 B1 | 6/2002 | Economikos et al. | |
| 6,448,131 B1 | 9/2002 | Cabral, Jr. et al. | |
| 6,495,411 B1 | 12/2002 | Mei | |
| 6,544,838 B2 | 4/2003 | Ranade et al. | |
| 6,555,430 B1 | 4/2003 | Chudzik et al. | |
| 6,734,056 B2 * | 5/2004 | Mandelman et al. | 438/212 |
| 2002/0106857 A1 | 8/2002 | Jammy et al. | |

\* cited by examiner

*Primary Examiner*—Chuong Anh Luu
(74) *Attorney, Agent, or Firm*—Joseph P. Abate; Howard M. Cohn

(57) ABSTRACT

A trench capacitor with an isolation collar in a semiconductor substrate where the substrate adjacent to the isolation collar is free of dopants caused by auto-doping. The method of fabricating the trench capacitor includes the steps of forming a trench in the semiconductor substrate; depositing a dielectric layer on a sidewall of the trench; filling the trench with a first layer of undoped polysilicon; etching away the first layer of undoped polysilicon and the dielectric layer from an upper section of the trench whereby the semiconductor substrate is exposed at the sidewall in the upper section of the trench; forming an isolation collar layer on the sidewall in the upper section of the trench; and filling the trench with a second layer of doped polysilicon.

4 Claims, 7 Drawing Sheets

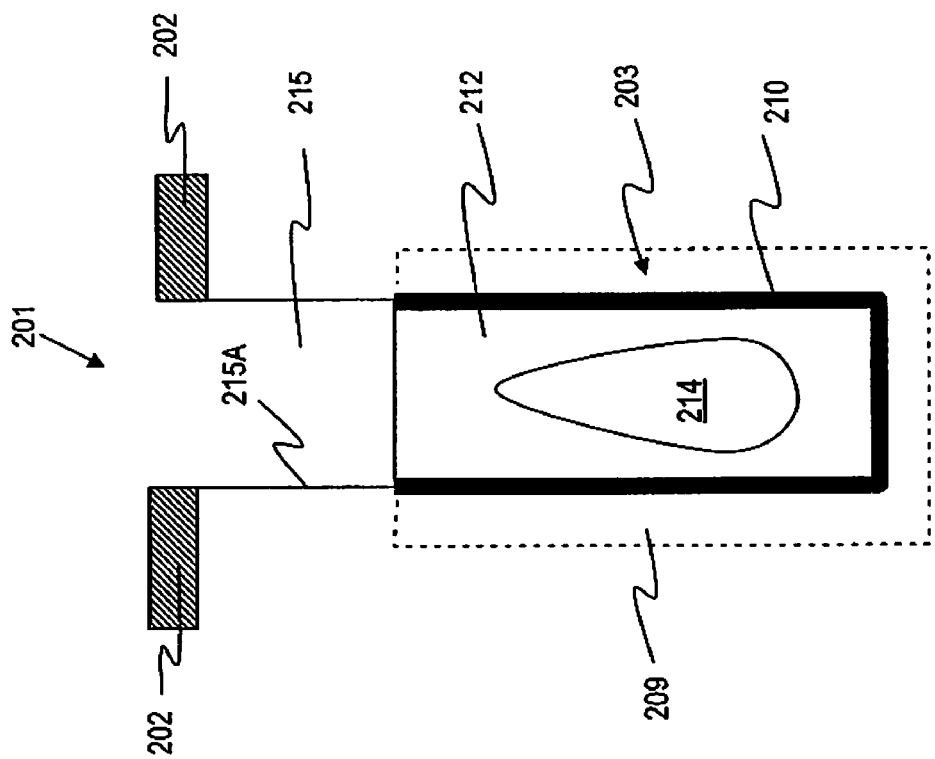
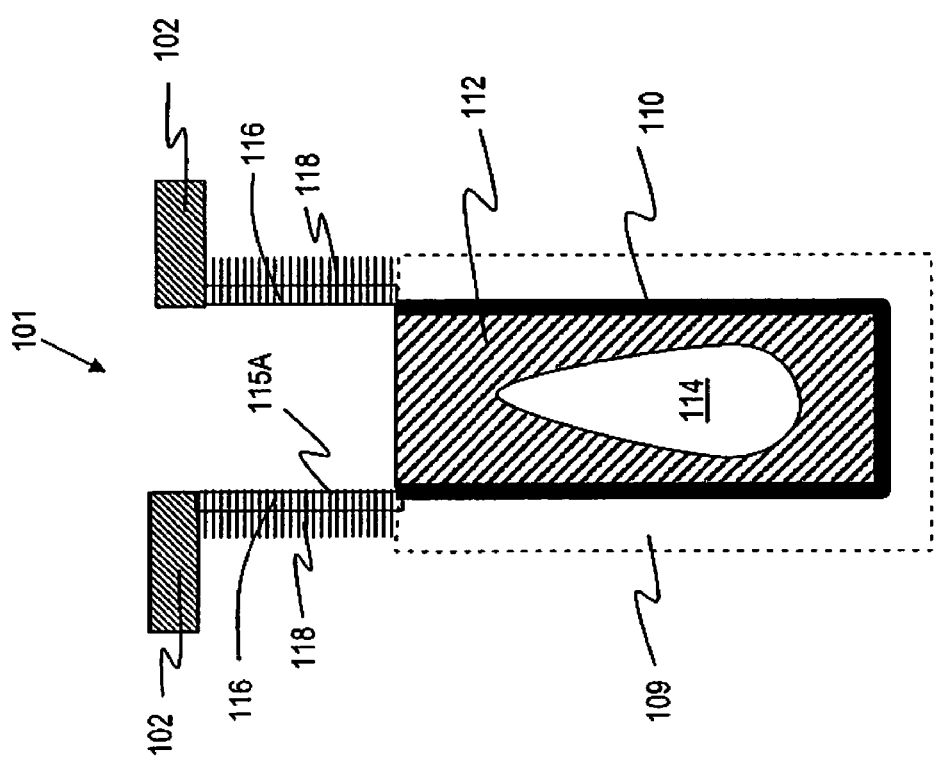

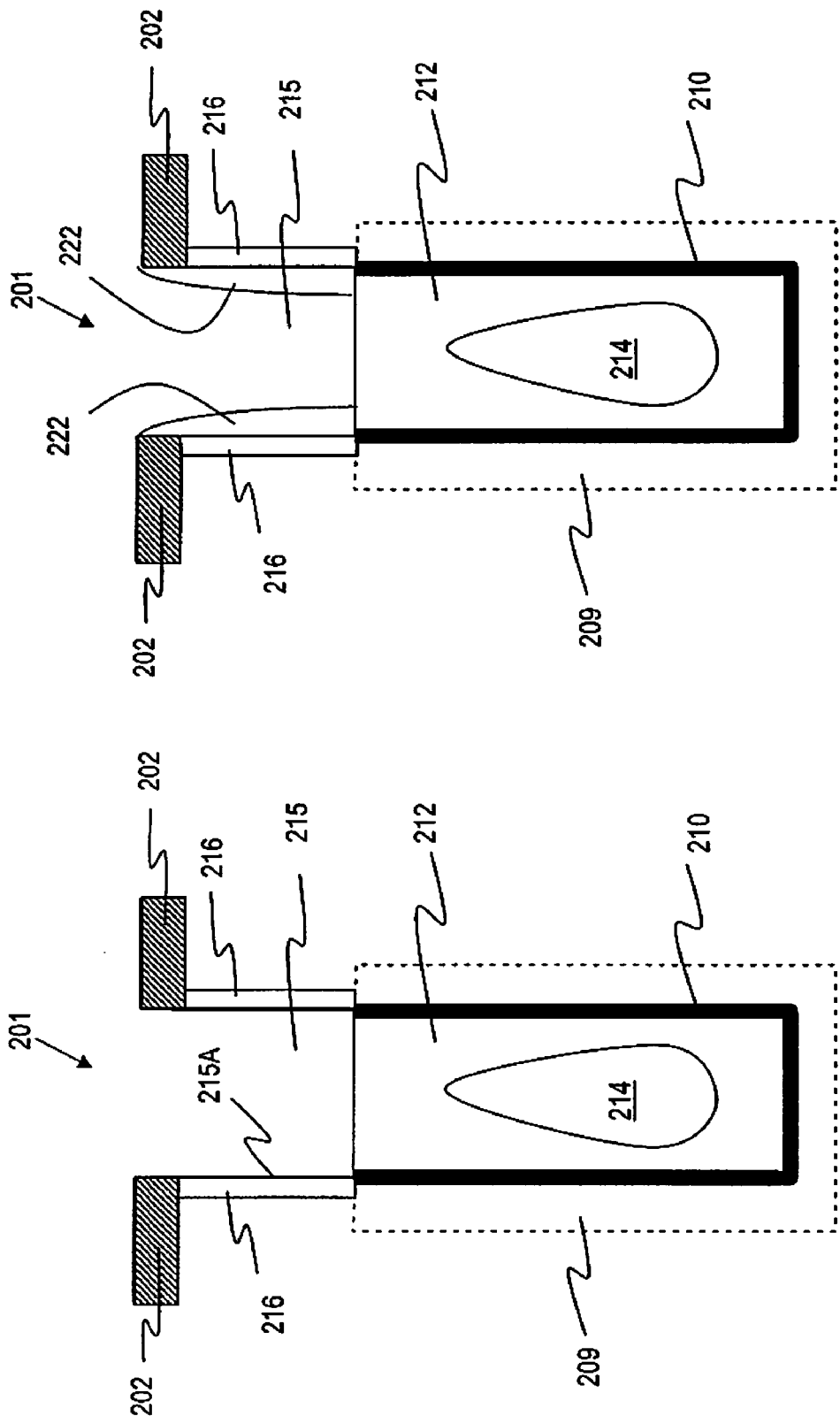

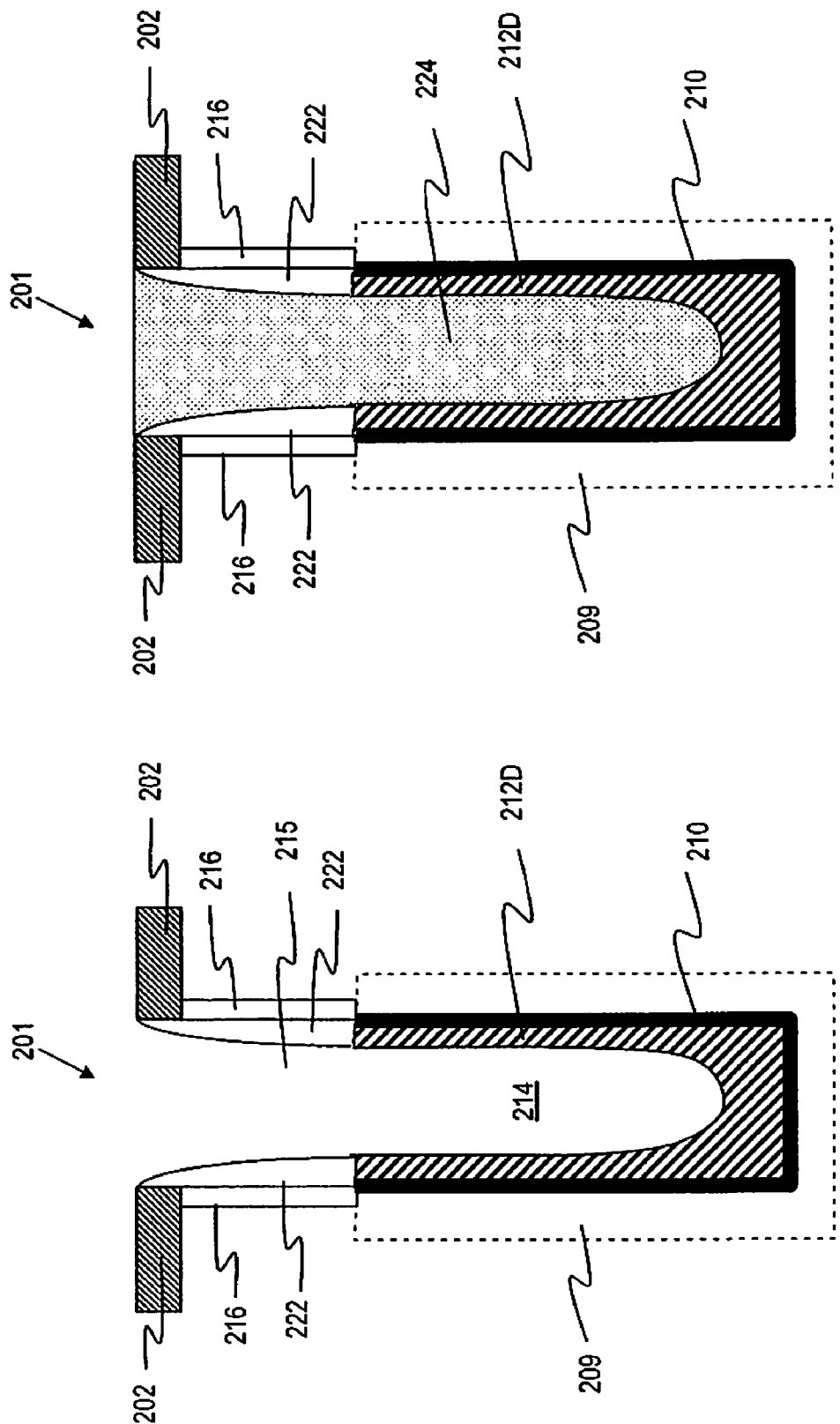

TRENCH CAPACITOR

CROSS REFERENCE TO RELATED APPLICATIONS

This application is a division of commonly-owned, U.S. patent application Ser. No. 11/380,693 filed on entitled A TRENCH CAPACITOR AND METHOD FOR FABRICATING THE SAME, and filed on Apr. 28, 2006 Now it is U.S. Pat. No. 7,410,862.

FIELD OF THE INVENTION

The present invention relates generally to a method of fabricating a semiconductor device. More particularly, the present invention relates to a trench capacitor and method of fabricating a trench capacitor that can be formed in a dynamic random access memory cell.

BACKGROUND

Trench capacitors are widely used in Dynamic Random Access Memory (DRAM) devices for data storage. A trench DRAM cell consists of a trench capacitor and a transistor. The trench capacitor typically consists of a hole etched into the substrate, a first electrode—often referred as a "buried plate"—in the substrate, a second electrode in the trench, and a thin storage-node dielectric which separates those two electrodes. The transistor is formed above the trench capacitor. A dielectric isolation collar is formed in the upper region of the trench to suppress undesired parasitic leakage current between the transistor and the capacitor.

A buried plate is formed in the substrate adjacent the trench by out-diffusing a dopant such as arsenic (As) into the substrate. Buried plate doping may be formed by conventional solid phase doping processes such as out-diffusing arsenic from a layer of arsenic-doped silicon glass (ASG) on trench sidewall, liquid phase doping, gas phase doping (GPD), plasma doping, plasma immersion ion implantation, infusion doping, or any combination of these methods that are well known in prior art. Trench capacitance enhancement may be optionally practiced before or after buried plate formation. The trench enhancement approaches may include forming a bottle-shape in the lower trench, roughening the lower trench by forming hemispherical silicon grains on the lower trench surface, or any other trench capacitance enhancement methods known in prior art. See, for example, U.S. Pat. Nos. 6,544,838; 6,495,411; 6,403,412; 6,190,988; 5,849,638; 6,448,131; and 6,555,430, all of which are included in their entireties herein by reference, for methods of enhancing trench surface and thus trench capacitance.

A bottle-shaped trench is formed by widening the dimensions of the bottom portion of the trench to form a bottle-shaped trench. The capacitance of a trench capacitor, to be formed thereafter along the bottom portion of the trench, is enhanced when the bottom portion is widened. Methods for forming a bottle-shaped trench are well known in the art. See, for example, U.S. Pat. Nos. 5,891,807; 6,190,988; 6,232,171; 6,403,412; and 6,544,838, all of which are included in their entireties herein by reference.

The node dielectric may be any suitable dielectric material, including but not limited to silicon oxide, silicon nitride, silicon oxynitride, aluminum oxide, combinations of these dielectric materials, or another high-k material. The node dielectric may be formed by any suitable process, including but not limited to, chemical vapor deposition (CVD), thermal oxidation, thermal nitridation, atomic layer deposition (ALD). For example, the node dielectric layer may comprise silicon nitride formed by LPCVD followed by a high temperature anneal (e.g., 800-1100° C.) in an environment containing oxygen.

The capacitor electrode in the trench usually consists of heavily doped polycrystalline silicon (polysilicon). The isolation collar process, which usually comprises a high-temperature oxidation step, is generally performed after the trench is filled with heavily doped polysilicon and the polysilicon is recessed to a predetermined depth.

During the high-temperature isolation collar process of forming a trench capacitor, the upper trench sidewall is exposed to the heavily doped polysilicon residing in the lower trench. Dopants are driven out from the heavily doped polysilicon in the lower trench. Some dopants diffuse into the substrate where the isolation collar is formed, causing undesirable doping in the substrate next to the isolation collar, referred to as auto-doping. Auto-doping increases parasitic leakage current and thus degrades the device characteristics.

Therefore, it is desired to have a structure and a process for forming a trench capacitor without suffering from the auto-doping problem.

SUMMARY OF THE INVENTION

According to the present invention, there is disclosed a method of fabricating a trench capacitor. The method comprises: providing a semiconductor substrate; forming a trench in the semiconductor substrate; depositing a dielectric layer on a sidewall of the trench; filling the trench with a first layer of undoped polysilicon; etching away the first layer of undoped polysilicon and the dielectric layer from an upper section of the trench whereby the semiconductor substrate is exposed at the sidewall in the upper section of the trench; forming an isolation collar layer on the sidewall in the upper section of the trench; and filling the trench with a second layer of doped polysilicon.

Further according to the present invention, the undoped polysilicon in a lower section of the trench is doped after the isolation collar is formed in the upper section of the trench.

According to the present invention, the step of doping the undoped polysilicon layer is performed with a solid phase doping process, a liquid phase doping process, a gas phase doping process, a plasma doping process, a plasma immersion ion implantation process, or an infusion doping process.

Still further according to the present invention, a buried doped plate is formed in the substrate adjacent to the lower section of the trench.

Still further according to the present invention, the isolation collar layer is formed of a first layer of oxide; and if desired, can include a second layer of oxide on the first oxide layer of the isolation collar.

Further according to the present invention, the step of filling the trench with an undoped polysilicon layer creates a cavity within the undoped polysilicon layer. The undoped polysilicon layer directly above the cavity can be removed to form a closed ended cavity that extends through the upper section of the trench so that the cavity is opened through the pad layer; and the trench is filled with a second doped polysilicon layer to form a trench capacitor with improved performance characteristics.

Also, according to the present invention, the step of removing the undoped polysilicon layer is performed with a reactive ion etch with an etchant of $SF_6$ and $CF_4$.

Also, according to the present invention, the step of removing the undoped polysilicon layer is performed with a wet etch process with an etchant containing ammonia, or an etchant containing hydrofluoric acid and nitric acid.

According to the present invention, a semiconductor device comprises a semiconductor substrate having at least one trench capacitor etched therein. The trench capacitor has an isolation collar and the substrate adjacent to the isolation collar being free of dopants caused by auto-doping. The trench capacitor comprises a first polysilicon layer disposed in a lower section of the trench capacitor, and a second polysilicon layer in the upper section of the trench capacitor.

Also according to the present invention, the trench capacitor comprises a first polysilicon layer having an open cavity therein, and a second polysilicon layer filling the open cavity.

BRIEF DESCRIPTION OF THE DRAWINGS

The structure, operation, and advantages of the present invention will become further apparent upon consideration of the following description taken in conjunction with the accompanying figures (Figs.). The figures are intended to be illustrative, not limiting.

Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

Figure 1A:
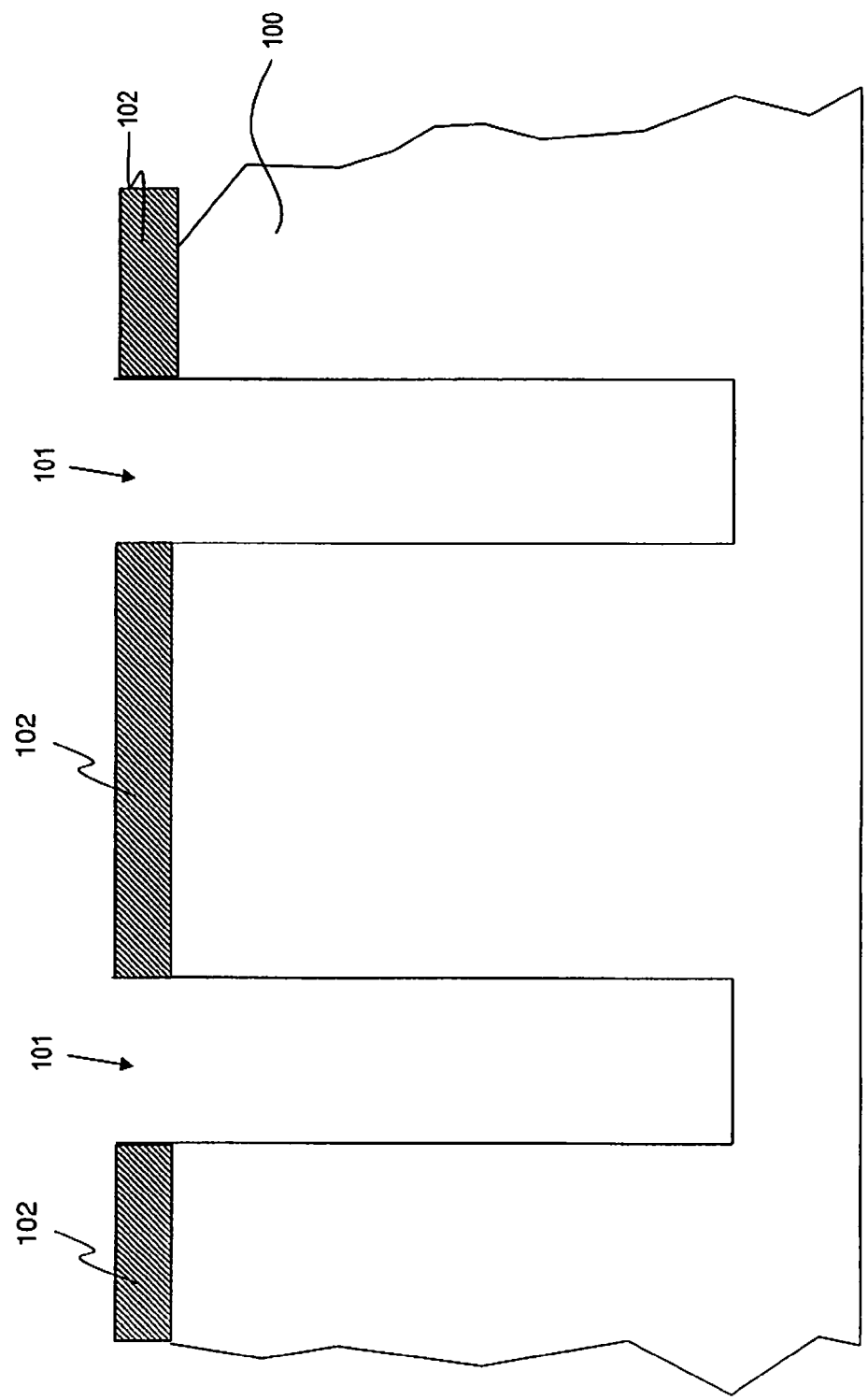

In the drawings accompanying the description that follows, often both reference numerals and legends (labels, text descriptions) may be used to identify elements. If legends are provided, they are intended merely as an aid to the reader, and should not in any way be interpreted as limiting.

FIG. 1A shows trenches formed in a semiconductor substrate.

Figure 1C:
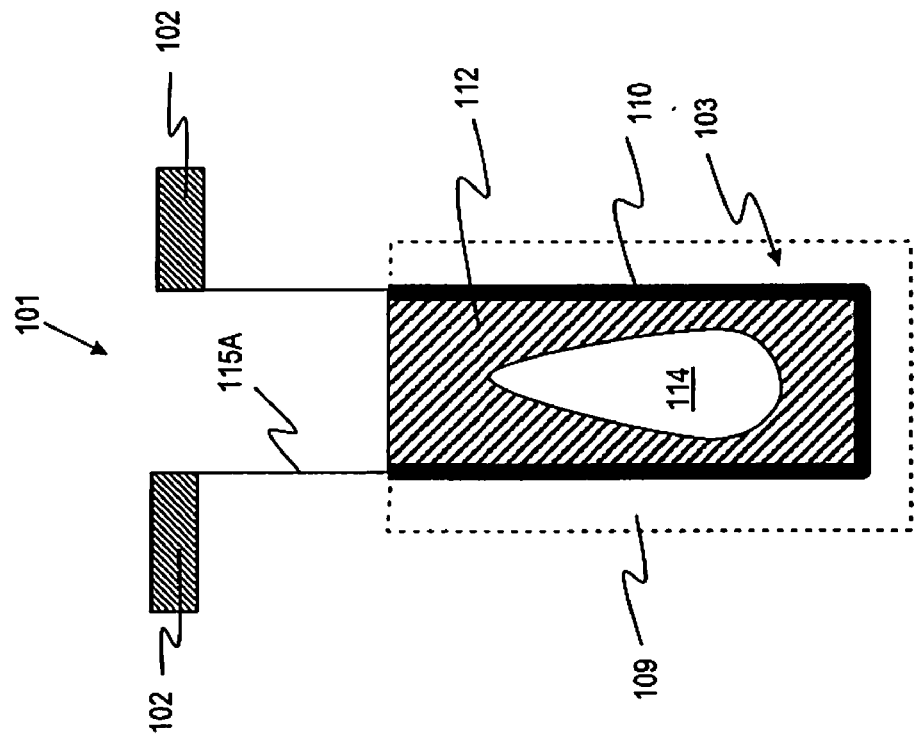
Figure 1B:
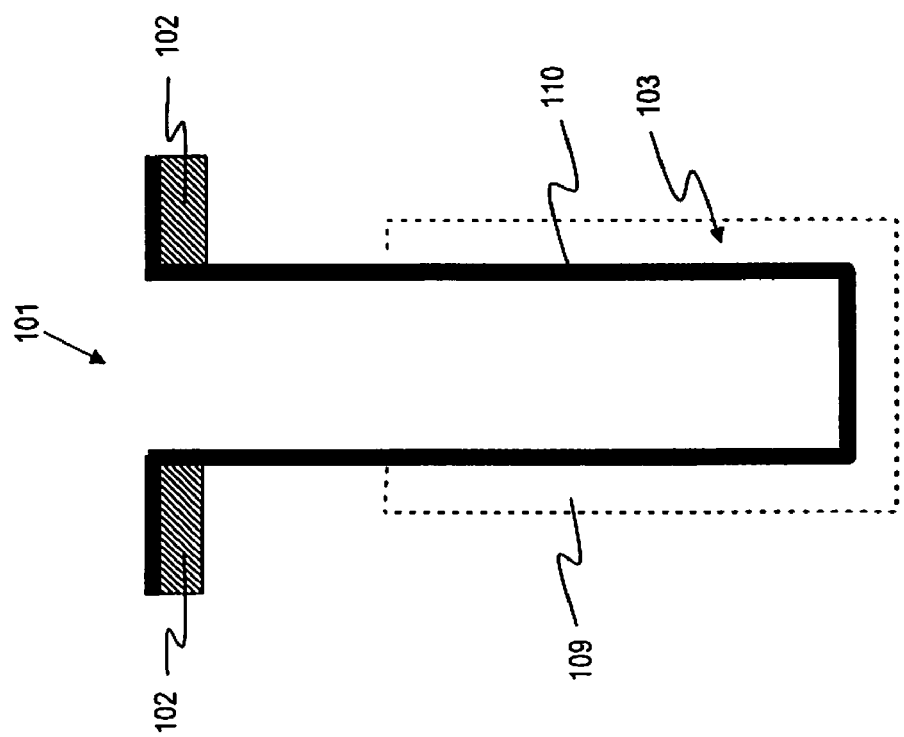

FIG. 1B shows a trench of FIG. 1A, with a buried plate formed in the lower trench and a dielectric material formed atop the entire substrate and inside the trench FIG. 1C shows the trench of FIG. 1B, with the lower trench filled with doped polysilicon.

FIG. 1D illustrates the undesirable auto-doping.

FIG. 2A illustrates a lower trench filled with undoped polysilicon.

FIG. 2B illustrates isolation collar oxidation.

FIG. 2C illustrates thickening the isolation collar by deposition.

Figure 2D:
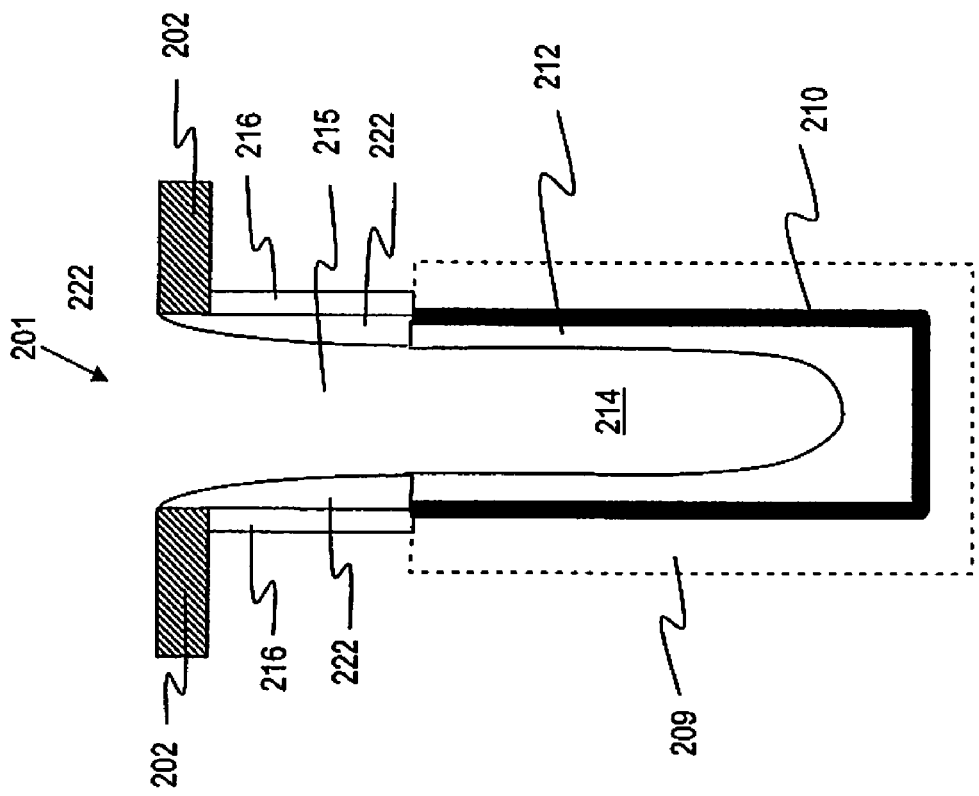

FIG. 2D illustrates an open cavity.

FIG. 2E illustrates the doping of the polysilicon in the lower trench.

FIG. 2F illustrates the filling of the trench with a second layer of polysilicon.

Figure 3:
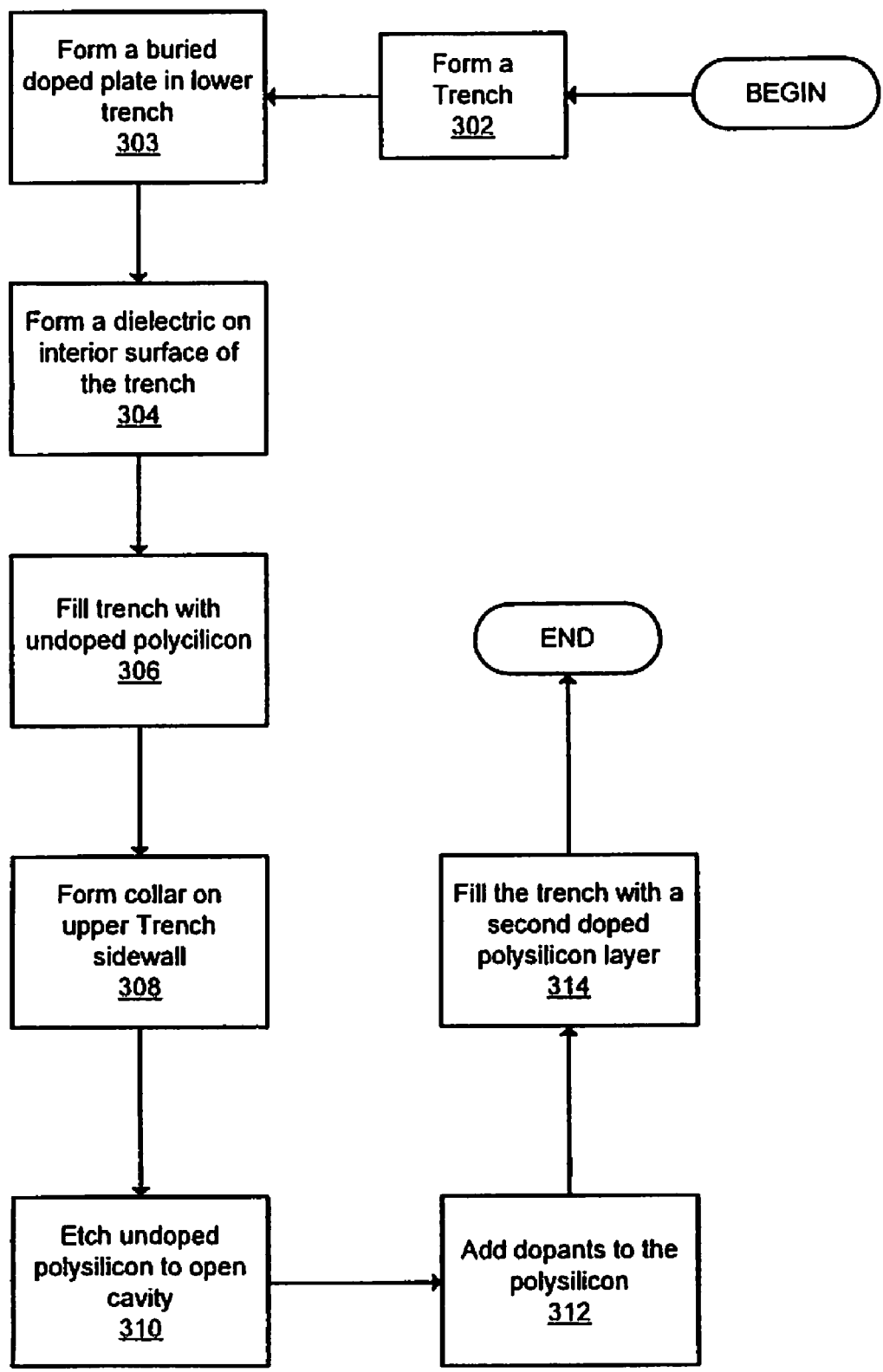

FIG. 3 is a flowchart indicating the steps of the method of the present invention.

DETAILED DESCRIPTION OF PREFERRED EMBODIMENTS

A critical distinction between the present invention and the prior art is that in prior art, a trench capacitor created in a semiconductor substrate to act as capacitor is filled with doped polysilicon before a dielectric isolation collar is formed in the upper region of the trench close to the surface of the substrate through which the trench is formed. During isolation collar formation, high temperatures cause dopants to be driven out from the doped polysilicon and into the substrate adjacent the isolation collar, referred to as auto-doping.

In the present invention, the trench formed to create a trench capacitor is filled with undoped polysilicon before the isolation collar is formed. In this way, no auto-doping occurs during the process of forming the isolation. The undoped polysilicon is then doped after the isolation collar has been formed.

Referring now to the figures, and more specifically to FIG. 1A, a cross sectional view of semiconductor substrate 100 is shown with a plurality of trenches 101. Each trench 101 forms a capacitor upon completion of the method of the present invention. At the top of substrate 100 is pad layer 102. Pad layer 102 usually comprises silicon nitride and an optional underlying silicon oxide.

FIG. 1B shows additional detail of trench 101. A buried doped region 109—often referred as buried plate—is formed in the semiconductor substrate 101 (FIG. 1A) adjacent to a lower section 103 of the trench 101. The buried doped plate 109 serves as an electrode of the trench capacitor when the process is complete. A dielectric layer 110 is formed on interior surface of the trench 101.

Referring now to FIG. 1C, the lower section 103 of trench 101 is filled with doped polysilicon 112. The doped polysilicon serves as the second electrode of the trench capacitor when the manufacturing process is complete. Depending on the trench shape and filling technique, a cavity 114 may be formed within the lower section 103 of the trench 101. The doped polysilicon 112 is then recessed, typical by reactive ion etch (RIE) to a predetermined depth. The exposed node dielectric 110 in the upper section 115 of trench 101 is then removed to expose the sidewall 115A of the upper section of the trench.

FIG. 1D shows what happens during the process of forming isolation collar 116 using prior art methods. A high-temperature process, typically ranging from about 800° C. to 1200° C. (degrees Celsius), is used to form oxidation collar 116 on the sidewall 115A of upper trench 115. During the high-temperature process, particularly at the beginning of process, dopants diffuse from the doped polysilicon 112, and penetrate into the substrate adjacent from the sidewall 115A of upper trench 115 and outward from the isolation collar 116 to form an undesired auto-doped region 118.

Up until now, the discussion of the figures has been about the prior art method. Now, FIG. 2A shows a step of the method of the present invention which corresponds to the step illustrated in FIG. 1C. However, unlike FIG. 1C, in FIG. 2A, the trench 201 is filled with undoped polysilicon 212. The undoped polysilicon 212 is different than doped polysilicon 112 in that virtually no dopants are present in undoped polysilicon 212. Depending on the trench shape and filling technique, a void or cavity 214 may form within the undoped polysilicon 212 in the lower section 203 of trench 201. The undoped polysilicon 212 and dielectric layer 210 are then removed from the sidewall 215A in the upper section 215 of trench 201. In one embodiment, the removal of the undoped polysilicon 212 includes a plasma etching process or a reactive ion etching process with an etchant containing $SF_6$ and $CF_4$. In one embodiment, the removal of the node dielectric layer 210 includes a wet etching process with an etchant containing a mixture of hydrofluoric/ethylene glycol (HF/EG). The upper section 215 extends through the pad layer 202 at the top of substrate 200.

In FIG. 2B, oxide isolation collar 216 is formed along the sidewalls 215A of the upper trench 215 by a thermal oxidation process in an environment containing at least one oxygen species selected from the group consisting of oxygen ($O_2$), nitrous oxide ($N_2O$) nitric oxide (NO), water ($H_2O$) and heavy water ($D_2O$). The oxidation process may include other species such as hydrogen ($H_2$), deuterium ($D_2$), nitrogen ($N_2$), argon (Ar), helium (He), etc. The oxidation process can be performed in an oxidation furnace or in a rapid thermal oxidation chamber. The oxidation temperature ranges from about 800° C. to 1200° C. (degrees Celsius) and the oxidation duration ranges from 30 seconds to 90 minutes. Note that no auto-doping occurs because the polysilicon 212 in trench 201 is undoped.

In FIG. 2C, optionally, the isolation collar 216 is further thickened by depositing an oxide layer 222 on the oxide isolation collar 216. The oxide layer 222 can be deposited by any suitable deposition process, including but not limited to, low-pressure chemical vapor deposition (LPCVD), plasma-enhanced chemical vapor deposition (PECVD), atmospheric pressure chemical vapor deposition (APCVD), rapid thermal chemical vapor deposition (RTCVD), high-density plasma chemical vapor deposition (HDPCVD), ozone tetra-ethyl-ortho-silicate (O3/TEOS) deposition, atomic layer deposition (ALD), etc.

In FIG. 2D, the undoped polysilicon 212 is etched away directly above the cavity 214, forming a closed end cavity 214A that extends through upper trench 215 so that cavity 214A is opened through the pad layer 202. The cavity 214A is preferably opened by a plasma, RIE, or wet etching process. Note that the process for opening the cavity 214 is optional. When it is omitted, cavity 214 remains closed.

In one embodiment, the cavity 214 is opened by a reactive ion etching process with an etchant of $SF_6$ and $CF_4$. In an alternative embodiment, the cavity 214 is opened by a wet etching process with an etchant containing ammonia or a mixture of hydrofluoric acid and nitric acid.

In FIG. 2E, optionally, the undoped polysilicon 212 of FIG. 2D is doped, forming doped polysilicon 212D. The undoped polysilicon 212 can be doped by any suitable doping process such as gas phase doping (GPD), plasma doping, plasma immersion ion implantation, infusion doping, out-diffusing dopants from a layer of doped material (not shown), or any combination of these methods that are well known in the art. If the optional process for opening cavity 214 is omitted and cavity 214 remains closed, undoped polysilicon 212 can still be doped as dopants diffuse from the dopant source into undoped polysilicon 212, for example, through polysilicon grain boundaries.

In FIG. 2F a second layer 224 of doped polysilicon is deposited in the trench 201, filling the entire open cavity 214A (FIG. 2E) to the opening through pad 202. The second layer of doped polysilicon 224 may be leveled via etching or polishing to be flat, just coplanar or slightly below the top of the pad layer 202. If the optional process for doping undoped polysilicon 212 is omitted, doped polysilicon 224 acts as dopant source to provide dopants which can diffuse into the undoped polysilicon 212, for example, through polysilicon grain boundaries.

Additional processes (not shown) can be further performed to form any semiconductor device based on the structure shown in FIG. 2F.

In one embodiment, the undoped polysilicon layer (212 of FIG. 2D) and the doped polysilicon 224 are deposited in a LPCVD (low pressure chemical vapor deposition) furnace using silicon precursors such as $SiCl_4$, $SiHCl_3$, $SiH_2Cl_2$, and $SiH_4$. Preferably, the deposition temperature ranges from about 450° C. to about 700° C., and more preferably from about 500° C. to about 550° C. The polysilicon thickness is sufficient to fill the trench 201. There is no dopant species present during deposition of the undoped polysilicon. The doped polysilicon can be deposited in an in-situ doped polysilicon deposition furnace by mixing silicon precursors with a hydride dopant gas such as $PH_3$ or $AsH_3$ for n-type doping and $B_2H_6$, $B_5H_9$, $B_{10}H_{14}$ for p-type doping. Alternatively, the doped polysilicon is deposited by repeatedly depositing an undoped polysilicon layer followed by a doping step. The undoped polysilicon layer (212 of FIG. 2D) and the doped polysilicon 224 ca deposited can also be deposited by other processes such as RTCVD (rapid thermal chemical vapor deposition), ALD (atomic layer deposition), etc.

FIG. 3 is a flowchart indicating the steps of the method of the present invention.

In step 302 a trench 201 is formed in a semi-conductor substrate 100, typically via reactive ion etching. In step 303, a buried doped plate 209 is formed in the semiconductor substrate adjacent to a lower section 203 of the trench 201. In step 304, a dielectric layer 210 is formed on the interior surface of trench 201. In step 306, the trench 201 is filled with undoped polysilicon. This is a critical distinction from the prior art, and provides the advantage of avoiding the effects of auto-doping during the isolation collar process. In step 308, an oxide isolation collar 216 is formed on the sidewalls 215A of the upper section 215 of trench 201 above the lower section 203 of the trench 201 that is filled with undoped polysilicon. In optional step 310 a cavity 114 that may have been formed when the undoped polysilicon that was deposited in the trench 201, is opened through the upper section 215 and the pad layer 202 of substrate 100. In optional step 312, the undoped polysilicon in the lower section of the trench is doped by any suitable doping process. In step 314, the open cavity 214A, extending through the upper trench 215 is filled with a second doped polysilicon.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, circuits, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

What is claimed is:

1. A semiconductor device comprising a semiconductor substrate, said substrate having a trench capacitor formed therein, the trench capacitor comprising a trench etched into the substrate, a buried plate first electrode in the substrate adjacent the trench, a second electrode disposed in the trench, and a thin storage-node dielectric which separates the two electrodes, the second electrode comprising:

a first undoped polysilicon layer disposed in a lower section of the trench; and a second doped polysilicon layer in an upper section of the trench;

wherein the first undoped polysilicon layer has an open cavity therein, and the second doped polysilicon layer fills the open cavity.

2. The semiconductor device of claim 1, wherein a top surface of the second polysilicon layer is flat.

3. The semiconductor device of claim 1, wherein a pad layer is disposed on a surface of the substrate, and the second polysilicon layer is leveled to be coplanar with a top of the pad layer.

4. The semiconductor device of claim 1, further comprising:
   a dielectric isolation collar formed in an upper region of the trench.

* * * * *